US010564085B2

(12) United States Patent
Löffler-Mang et al.

(10) Patent No.: US 10,564,085 B2
(45) Date of Patent: Feb. 18, 2020

(54) DEVICE AND METHOD FOR MEASURING PRECIPITATION

(71) Applicant: KISTERS AG, Aachen (DE)

(72) Inventors: Martin Löffler-Mang, Karlsruhe (DE); Manuel Del Fabro, Saarbrücken (DE)

(73) Assignee: KISTERS AG, Aachen (DE)

( * ) Notice: Subject to any disclaimer, the term of this patent is extended or adjusted under 35 U.S.C. 154(b) by 144 days.

(21) Appl. No.: 15/742,251

(22) PCT Filed: Jul. 6, 2016

(86) PCT No.: PCT/DE2016/100299
§ 371 (c)(1),
(2) Date: Jan. 5, 2018

(87) PCT Pub. No.: WO2017/005250
PCT Pub. Date: Jan. 12, 2017

(65) Prior Publication Data
US 2018/0238787 A1    Aug. 23, 2018

(30) Foreign Application Priority Data
Jul. 6, 2015  (DE) ........................ 10 2015 110 826

(51) Int. Cl.
*G01W 1/14*  (2006.01)
*G01N 15/00* (2006.01)
(Continued)

(52) U.S. Cl.
CPC ..... *G01N 15/0205* (2013.01); *G01N 15/0227* (2013.01); *G01W 1/14* (2013.01);
(Continued)

(58) Field of Classification Search
CPC .. G01N 15/0205; G01N 15/0227; G01W 1/14
See application file for complete search history.

(56) References Cited

U.S. PATENT DOCUMENTS 5,090,808 A * 2/1992 Ishikawa ............ G01N 15/0205
                                              250/574
5,880,836 A * 3/1999 Lonnqvist ............... G01S 17/95
                                              356/336
(Continued)

FOREIGN PATENT DOCUMENTS

CN    103033857 A    4/2013
DE    19724364 A1   12/1998
(Continued)

OTHER PUBLICATIONS

Anton Kruger et al: "Two-Dimensional Video Disdrometer: A Description", Journal of Atmospheric and Oceanic Technology, vol. 19, No. 5, May 1, 2002 (May 1, 2002), pp. 602-617, XP055264367.

(Continued)

*Primary Examiner* — Thanh Luu
(74) *Attorney, Agent, or Firm* — Lucas & Mercanti, LLP; Klaus P. Stoffel

(57) ABSTRACT

A device and method for measuring precipitation, in particular snowfall or hail, which has a measuring chamber for receiving a precipitation particle, at least one light source for radiating the measuring chamber with light, and at least one sensor for sensing an intensity of the light radiating through the measuring chamber. At least two measurement areas, which are arranged one below the other, are provided in the measuring chamber, and the intensity of the light radiating through each of the measurement areas can be detected separately.

17 Claims, 4 Drawing Sheets

(51) Int. Cl.
*G01N 15/02* (2006.01)
*G01N 15/10* (2006.01)

(52) U.S. Cl.
CPC ............... *G01N 2015/0003* (2013.01); *G01N 2015/0046* (2013.01); *G01N 2015/025* (2013.01); *G01N 2015/1075* (2013.01)

(56) References Cited

U.S. PATENT DOCUMENTS

| 8,345,236 B2 * | 1/2013 | Dietrich | G01N 15/1429 |
| | | | 356/335 |
| 2015/0035944 A1 | 2/2015 | Gao | |

FOREIGN PATENT DOCUMENTS

| DE | 19911654 C1 | 12/2000 |
| DE | 102008041330 A1 | 2/2010 |
| DE | 102011101384 A1 | 11/2012 |
| KR | 101506838 B1 | 3/2015 |
| WO | 2005116610 A1 | 12/2005 |
| WO | 2006067513 A1 | 6/2006 |

OTHER PUBLICATIONS

Wu J: "Fast-Moving Suspended Particles: Measurements of Their Size and Velocity", Applied Optics, Optical Society of America, Washington, DC: US, vol. 16, No. 3, Mar. 1, 1977 (Mar. 1, 1977), pp. 596-600, XP002900247.

* cited by examiner (a)

(b)

DEVICE AND METHOD FOR MEASURING PRECIPITATION

The present application is a 371 of International application PCT/DE2016/100299, filed Jul. 6, 2016, which claims priority of DE 10 2015 110 826.7, filed Jul. 6, 2015, the priority of these applications is hereby claimed and these applications are incorporated herein by reference.

BACKGROUND OF THE INVENTION

The invention relates to a device for measuring precipitation, in particular snowfall or hail, which comprises a measuring chamber for receiving a precipitation particle, at least one light source for radiating light through the measuring chamber, and at least one sensor for sensing an intensity of the light radiating through the measuring chamber.

Furthermore, the invention relates to a method for measuring precipitation.

Such a device, which can be used to determine, inter alia, the size and the speed of precipitation particles, is known from DE 197 24 364 A1. What is disadvantageous is that the size and the speed are often ascertained erroneously particularly in the case of irregularly shaped precipitation particles.

SUMMARY OF THE INVENTION

The present invention is based on the object of providing a device of the type mentioned in the introduction which enables a more accurate measurement.

This object is achieved according to the invention by virtue of the fact that at least two measuring regions arranged one below another are provided in the measuring chamber and the intensity of the light radiating through each of the measuring regions is detectable separatable.

If the precipitation particle falls into the measuring chamber, upon passing through the measuring regions it prevents the light from penetrating completely from the light source to the sensor. The sensor then senses firstly for the upper measuring region, and afterward for the lower measuring region, a change in the light intensity, the temporal profile of which can preferably be determined by means of an evaluation unit. From the quotient of the vertical distance between the positions of the measuring regions and the time interval for sensing the changes in the light intensities for the measuring regions, the speed at which the precipitation particle falls through the measuring chamber can be ascertained by means of the evaluation unit.

The horizontal length, i.e. the width, of the precipitation particle upon passing through the measuring chamber can be determined on the basis of the magnitude of the change in intensity which is caused by virtue of the light impinging on the precipitation particle. The wider the precipitation particle, the more the sensor is darkened and a light intensity change of corresponding magnitude is sensed.

The vertical length, i.e. the height, of the precipitation particle upon passing through the measuring chamber can be ascertained by the duration of the light intensity change upon passing through at least one of the measuring regions being correlated with the falling speed ascertained in the manner as described above.

The determination according to the invention of the falling speed and also of the height and the width of the precipitation particle proves to be advantageous in particular for determining properties of snowflakes or hailstones because the heights and widths thereof differ from one another to a greater extent than those of raindrops, which when falling have a roundish shape, the shape of which is known depending on the size of the raindrops. The shapes of snowflakes, in particular, are highly variable on account of the many different crystal shapes that form.

Furthermore, the information obtained can be taken as a basis for making statements about how the precipitation particles become arranged on a substrate. In this regard, since a volume of the precipitation particles can be determined from the width and height and an amount of precipitation can be established on the basis of the frequency of detected precipitation particles, it is possible to determine a precipitation height becoming arranged on a substrate.

Furthermore, the ascertained volume and the ascertained falling speed of the precipitation particle can be taken as a basis for making statements about the density of said precipitation particle and, for snowflakes, if appropriate, statements about the moisture thereof. Therefrom in turn it is possible to ascertain a load exerted on the substrate by the fallen precipitation particles and/or information about a risk of avalanche.

While it would be conceivable to provide a dedicated light source for each of the measuring regions, in one configuration of the invention just a single light source is provided for the at least two measuring regions. The light emerging from the light source is directed by means of at least one optical component, e.g. a lens or a mirror, in such a way that it radiates completely through the at least two measuring regions. In particular, a light-emitting diode (LED) or a laser diode is suitable as the light source.

In one configuration of the invention the device is provided in such a way that the light radiates through the measuring regions in a horizontal direction, wherein the light beams emerging from the light source are preferably arranged parallel to one another in the measuring regions. While it would be conceivable to configure the device in such a way that all or some of the light beams radiate through the measuring regions transversely with respect to the horizontal, i.e. in a direction having horizontal and vertical direction components, in the preferred embodiment of the invention the device is provided in such a way that light is radiated through the measuring regions exactly in a horizontal direction.

In one embodiment of the invention, a sensor is provided for each of the measurement regions. However, it has proved to be particularly cost-effective for the production of the device for just a single sensor to be provided for the at least two measurement regions and for the light radiating through the regions to be directed onto the sensor by means of at least one further optical component. The sensor or sensors can be formed by a photocell, a photodiode, a phototransistor or by CMOS or CCD sensors.

The measurement regions are expediently formed by sections of the measuring chamber through which the light guided onto the sensor is radiated.

In one embodiment of the invention, provision is made of a diaphragm arranged in the beam path of the device, said diaphragm having a, preferably rectangular, aperture preferably for each of the measurement regions. The measurement regions are then formed by those sections in the measuring chamber through which the light guided right onto the sensor penetrates.

If the sensor, e.g. the CMOS sensor or the CCD sensor, comprises a plurality of sensor elements (pixels) which can sense the light intensity separately, the measurement regions can be formed by the light being sensed only in specific area sections, which can be formed for example by a plurality of rows—arranged directly one below another—of the sensor elements (pixel rows), which jointly form a rectangular shape.

While it would be conceivable to form the measurement regions one directly below another, in one preferred embodiment of the invention said measurement regions are arranged at a vertical distance from one another. Advantageously, the speed of the precipitation particle can thus be ascertained particularly precisely.

In a further configuration of the invention, the cross sections of the different measurement regions that are formed perpendicularly to the radiation direction are provided such that they are of different sizes, preferably on account of different heights and/or widths. This proves to be advantageous particularly if just a single sensor is provided for the at least two measurement regions. If the precipitation particle passes through the measurement region having a larger cross section, the intensity change ascertained is smaller than if the precipitation particle passes through the measurement region having a smaller cross section. On the basis of the temporal profiles of the intensity changes generated by the precipitation particle upon passing through the measurement regions, and/or on the basis of the known size ratios of the measurement region cross sections with respect to one another, the intensity changes can be assigned to a specific precipitation particle. Measurement errors owing to incorrect assignment can advantageously be avoided as a result, said measurement errors occurring in particular if two or more of the precipitation particles fall through the measurement regions at short time intervals relative to one another.

In a further configuration of the invention, as viewed in the light radiation direction, at least one of the measurement regions projects beyond the other measurement region horizontally, preferably on both sides, in order to avoid measurement errors caused by the precipitation particle falling through the measuring chamber at an edge of the measurement region and only partly passing through the measurement region ("marginal passage"). The precipitation particles are determined using only the measurements in which an attenuation of the intensity is generated in the two measurement regions by the precipitation particles. Particularly if one measurement region projects beyond the other to an extent such that the precipitation particle, even if it merely grazes the narrower measurement region, falls completely through the wider measurement region, it is ensured that the precipitation particle is sensed completely and thus correctly in the wider measurement region. It has proved to be suitable to allow the wider measurement region to project by at least 1 cm, preferably 2 cm, on each of the sides in order that even relatively large snowflakes can be measured as accurately as possible.

Advantageously, in the case of the sensors provided with the plurality of sensor elements (pixels), the marginal passages can be identified directly and measurement results obtained therefrom can be corrected or erased. Furthermore, such sensors make it possible to identify when a plurality of the precipitation particles fall simultaneously through the measurement regions. While a correction or erasure could be carried out in these cases, too, it would also be conceivable for the intensity changes generated by respective precipitation particles to be evaluated separately.

In one development of the invention, the device, for determining a standard signal generated by the light source on the sensor, comprises a light source sensor for determining the intensity of the light beams generated by the light source and/or a unit for measuring the temperature. The light source sensor is preferably arranged in such a way that it can measure the intensity of the light emerging from the light source directly, i.e. without optical components arranged between the light source and the light source sensor.

Advantageously, intensity changes which occur because the light intensity emitted by the light source changes can thereby be determined in order to avoid measurement errors. If, for time segments in which no precipitation falls into the measuring chamber, the intensity ascertained by means of the light source sensor correlates with that of the sensor for the measurement regions, it is possible to obtain information about an aerosol present in the measuring chamber, in particular fog, or/and about a covering of the optical components of the device, e.g. by dew, contamination or the precipitation itself. It goes without saying that a calibration measurement should be performed for this purpose when the optical components are uncovered and the measuring chamber is free of the precipitation particles.

The temperature measuring unit mentioned can be provided in order to monitor whether the ascertained properties of the precipitation particle can be reconciled with the respective local temperature.

In one embodiment of the invention, the device comprises at least one scattered light sensor for determining scattering of the light at the optical component or optical components, in particular at a window separating the measuring chamber, at said mirror or/and at said lens, on account of the covering. By virtue of the information obtained using the scattered light sensor, the intensity change caused by the scattering at the components can be differentiated from that caused by the aerosol. Errors during the measurement of the aerosol, in particular of fog, can advantageously be avoided as a result.

BRIEF DESCRIPTION OF THE DRAWING

The invention is explained in greater detail below on the basis of exemplary embodiments and with reference to the accompanying drawings relating to said exemplary embodiments, in which.

DETAILED DESCRIPTION OF THE INVENTION

Figure 1:
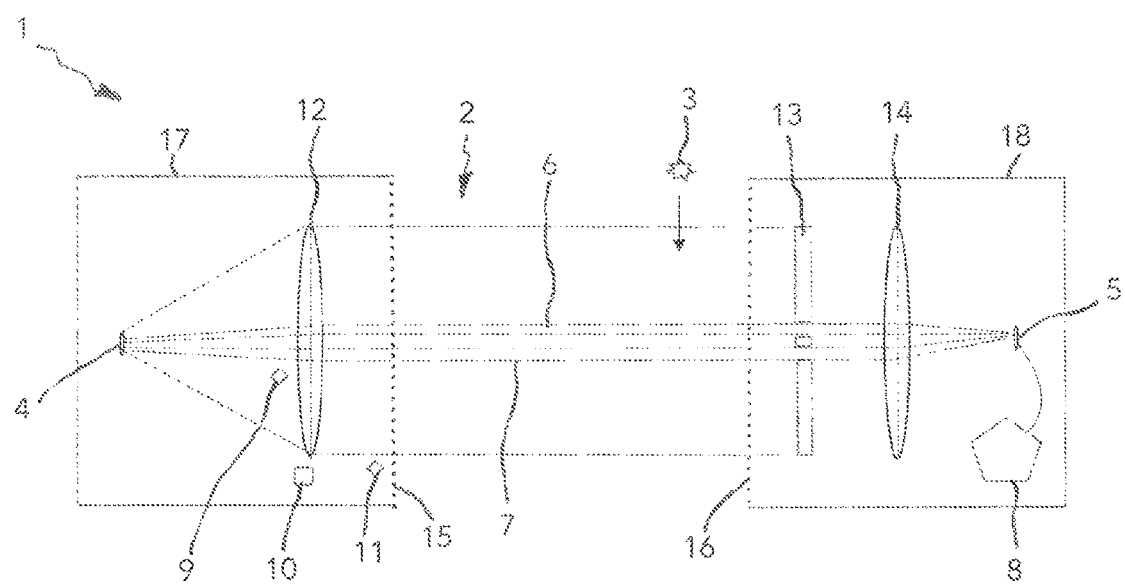
FIG. 1 schematically shows a device according to the invention and details of the device.
Figure 1:
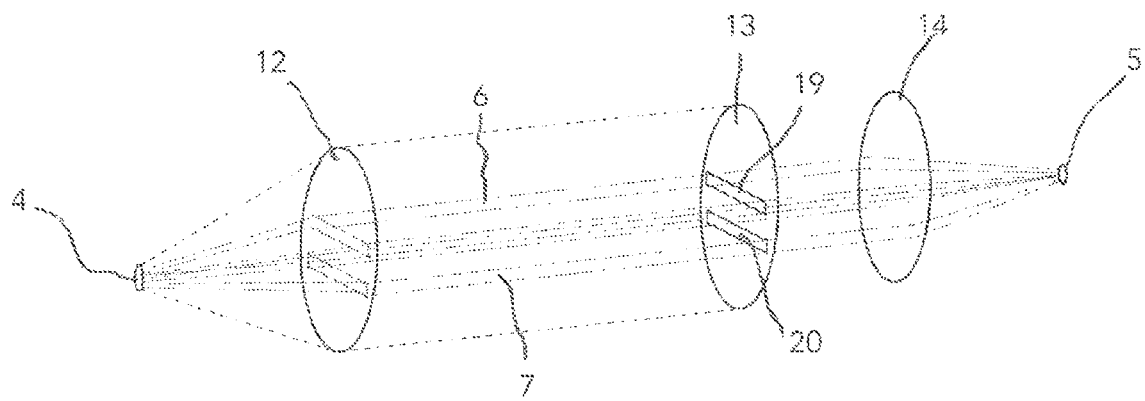
Figure 1:
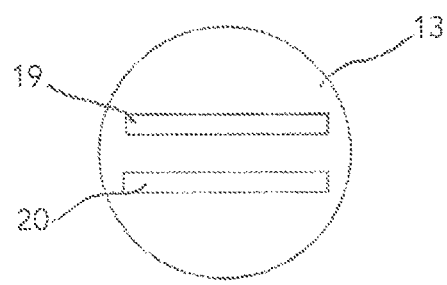

A device 1 shown in FIG. 1a comprises two housing parts 17, 18, between which a measuring chamber 2 is formed, which is provided for receiving falling precipitation particles 3. Arranged in the first housing part 17 are a light source 4, which can be formed e.g. by an LED, and a lens 12, which refracts light emerging from the light source 4 in such a way that light beams passing through the lens 12 pass through the measuring chamber 2 in the horizontal and also parallel to one another. In the housing part 17, which is provided with a transparent window pane 15 on its side facing the measuring chamber 2, there are furthermore arranged a light source sensor 9, which is provided for determining the light intensity emerging from the light source 4, a temperature sensor 10 and a scattered light sensor 11, by means of which light scattering caused by the window pane 15 can be ascertained.

In the second housing part 18, which is provided with a transparent window pane 16 on its side facing the measuring chamber 2, there is arranged a diaphragm 13 having two apertures 19, 20 having a rectangular cross section of the same size, said apertures being arranged one below the other. Downstream of the diaphragm 13 as viewed in the light radiation direction, there is arranged in the housing part 18 a lens 14, which refracts the light beams penetrating through the diaphragm 13 onto a light sensor 5, which can be formed e.g. by a photodiode. An evaluation unit 8 is connected to the light sensor 5, said evaluation unit being provided for receiving, storing and evaluating light intensities ascertained by means of the sensor 5. As shown in particular in FIG. 1b, which illustrates a beam path in the device 1, a measurement region 6 is formed by a part of the measuring chamber 2 which is illustrated by dashed lines in FIG. 1b and through which penetrate light beams passing through the measuring chamber 2 and the aperture 19 toward the sensor 5. A measurement region 7 is a part of the measuring chamber 2 through which light is radiated which penetrates through the measuring chamber 2 and the aperture 20 to the sensor 5.

Precipitation can be measured by means of the device 1 as explained below.

Figure 2:
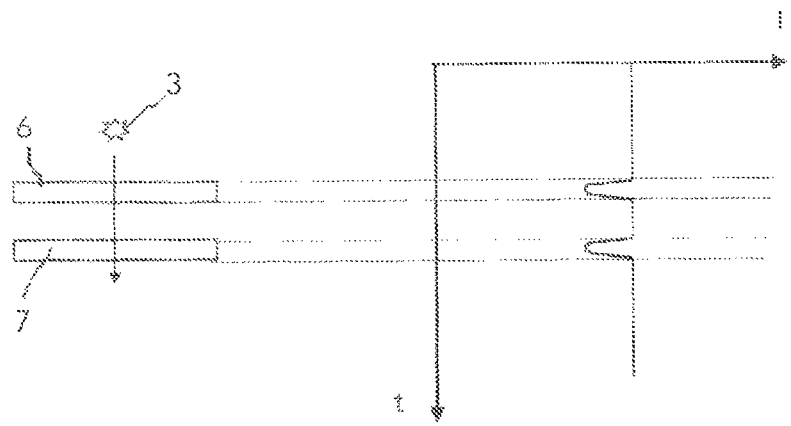
FIG. 2 shows details of a measurement by means of the device according to FIG. 1.

If a precipitation particle 3 falls through the measuring chamber 2, it enters firstly the measurement region 6 and then the measurement region 7. Upon entry into the first measurement region 6, by means of the sensor 5, as shown in FIG. 2, the reduction of the measured light intensity is sensed, said reduction being caused by virtue of the fact that the light beams emerging from the light source 4 impinge on the precipitation particle 3 and the light beams are thereby prevented from penetrating as far as the sensor 5. A magnitude of the reduction of the light intensity, which is determinable in FIG. 2 on the basis of an amplitude of a curve representing the change in the light intensity, allows a horizontal length of the precipitation particle 3, i.e. the width thereof, to be determined.

If the precipitation particle 3 then enters the measurement region 7, the light sensor 5 detects a reduction of the light intensity in the same way. The evaluation unit 8 ascertains the speed of the measurement particle from the time interval between the light intensity reduction in the first measurement region 6 and that in the second measurement region 7.

A vertical length, i.e. the height, of the precipitation particle can be determined according to the following formula: H=V*T−D, Wherein H=height of the precipitation particle 3, V=speed of the precipitation particle 3, T=duration of the light intensity reduction in one of the measurement regions 6, 7 and D=height of the respective measurement region 6, 7.

The device according to the invention can advantageously be used for measuring snowflakes since the latter, in particular, have heights and widths deviating from one another.

Furthermore, the device 11, in time periods in which the measuring chamber is free of precipitation particles, can be used for measuring aerosol.

To that end, the light intensity ascertained by means of the light source sensor 9 during a calibration measurement, wherein the windows 15, 16 are free of coverings of their surfaces and the measuring chamber 2 is empty, is correlated with the light intensity determined by means of the sensor 5 in order to determine an equipment-dictated deviation of the light intensities from one another that is cased by the windows 15, 16. Furthermore, effects of a covering of the window pane 15, 16 which are caused by dew or precipitation particles adhering to the window pane 15, 16, for example, on the measured light intensity can be ascertained by means of the scattered light sensor 11. If an aerosol, e.g. fog, is present in the measuring chamber 2, the light intensity ascertained by means of the sensor 5 decreases compared with that determined by the light source sensor 9. If that proportion of the reduction of the light intensity which is caused by the covering is taken into account in the evaluation of the measurement results of the light source sensor 9 and of the sensor 5, it is possible to determine an aerosol density, in particular a fog density, in the measuring chamber 2. By way of example, a visibility in fog can be determined therefrom by means of the device 1.

Figure 3:
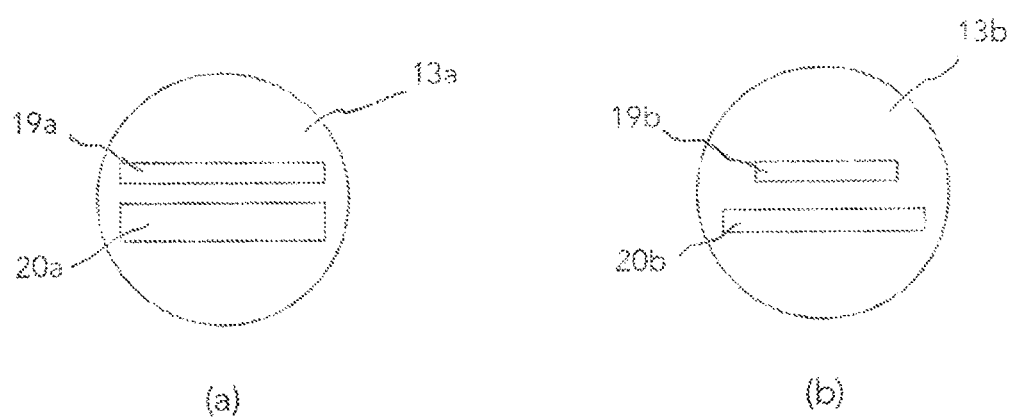
FIG. 3 shows different diaphragms for the device according to FIG. 1.
Figure 4:
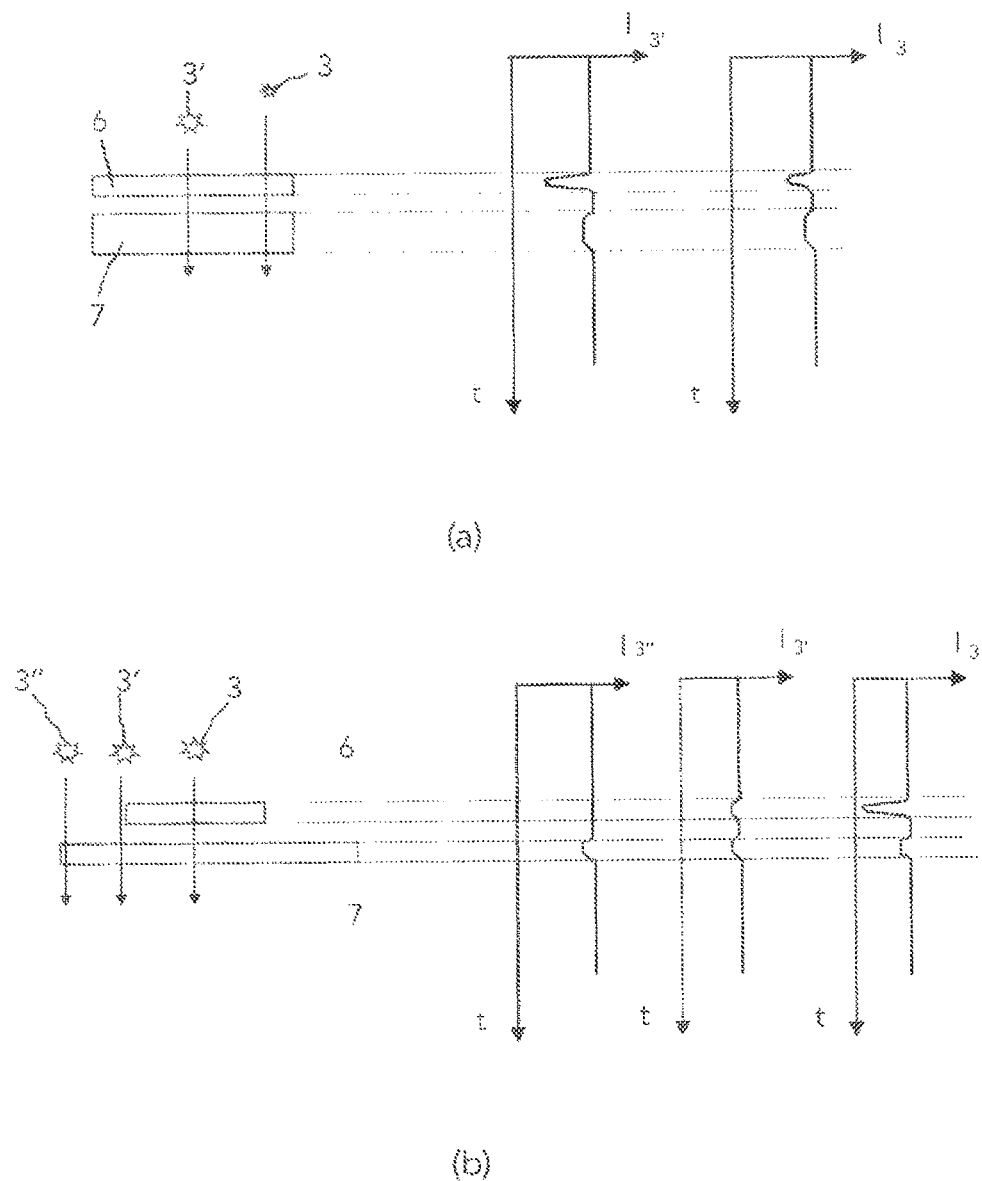
FIG. 4 shows details of measurements by means of the device according to FIG. 1 equipped with the diaphragms according to FIG. 3, and FIG. 5 schematically shows further devices according to the invention.
Figure 5:
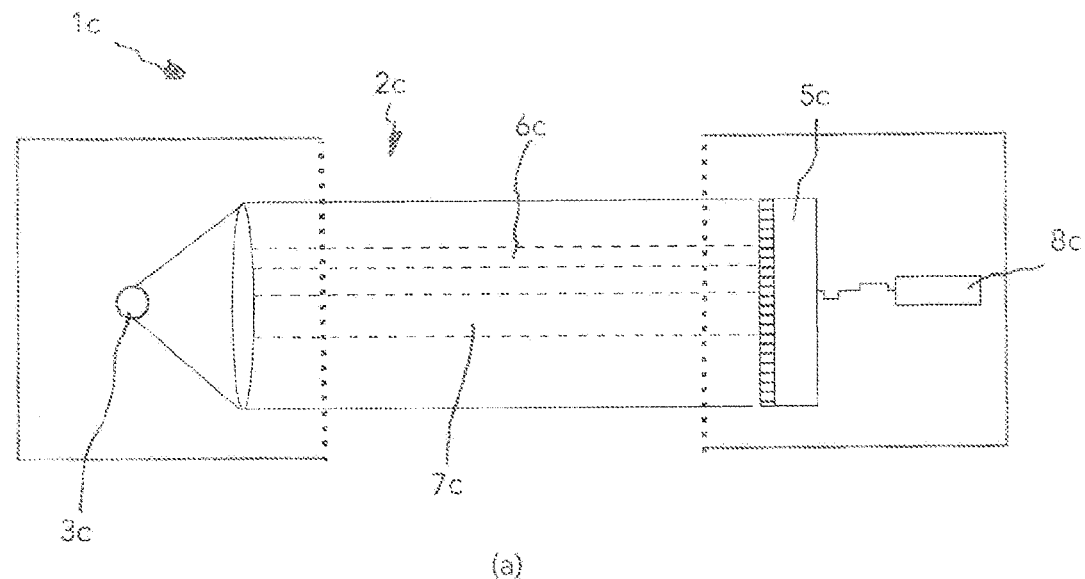
Figure 5:
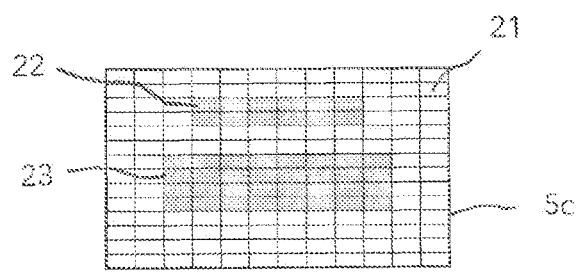

Reference will now be made to FIGS. 3 to 5, wherein identical or identically acting parts are designated by the same reference numeral as in FIGS. 1 and 2 and a letter is respectively attached to the relevant reference numeral.

FIG. 3a shows a diaphragm 13a having apertures 19a, 20a having a rectangular cross section, which have the same length in the horizontal direction and are arranged one below the other. The lower aperture 20a has a greater length in the vertical direction than the upper aperture 19a. The way in which the light intensity ascertained changes if, in the device 1 according to FIG. 1, the diaphragm 13a is used instead of the diaphragm 13 and the precipitation particle 3,3' falls through the measuring chamber 2 can be gathered from FIG. 4a. Since the cross-sectional area of the aperture 20a is greater than that of the aperture 19a, the light intensity reduction caused by the precipitation particle 3,3' is greater in the upper measurement region 6a compared with in the lower measurement region 7. Advantageously, the respectively ascertained reduction of the light intensity of the arrangement of the precipitation particle 3,3' can thereby be assigned unambiguously to the upper or lower measurement region 6, 7. This proves to be advantageous particularly if different precipitation particles 3,3' penetrate into the measuring chamber 2 successively at short time intervals, since an assignment of the respective precipitation particles 3,3' to the respective measurement regions 6,7 becomes possible on account of the differing profiles of the intensity changes.

In the case of a diaphragm 13b shown in FIG. 3b, apertures 19b, 20b of the diaphragm 13b differ in that the lower aperture 20b has a greater length than the aperture 19b in the horizontal direction and the aperture 20b projects beyond the aperture 19b on both sides in the horizontal direction. The measurement of the precipitation takes into account only precipitation particles 3,3' falling into the measuring chamber 2 which penetrate into measurement regions 6,7 formed both by the aperture 19b and by the aperture 20b and the determination of the width of the precipitation particle only takes into account the light intensity change caused by the precipitation particle 3,3' upon passing through the lower measurement region 7. The intensity change in the measurement region 7, said intensity change being caused by the precipitation particle 3'' that does not penetrate into the measurement region 6, is ignored. This ensures that the size of the precipitation particle 3,3' is always ascertained correctly. Incorrect measurements which may arise by virtue of the precipitation particle 3' only partly falling through the measurement regions 6,7 are avoided. If the length by which the lower aperture 20b projects beyond the upper aperture 19b on the respective sides is chosen with a magnitude such that the precipitation particle 3,3', if it only grazes the upper measurement region 6, always falls completely through the lower measurement region 7, it can be ensured that the precipitation particle 3,3' is always sensed completely in the lower measurement region.

FIG. 4b shows changes in the light intensity which are determined if the precipitation particle 3' only partly penetrates through the upper measurement region 6 and falls completely through the lower measurement region 7. The speed of the precipitation particle 3' can be determined on the basis of the time interval between the maxima of the intensity changes ascertained. The vertical and horizontal lengths of the precipitation particle 3' are ascertained in the manner as described above on the basis of the light intensity change in the lower measurement region 7, in which the precipitation particle 4 is sensed completely.

FIG. 5 shows a further device is according to the invention, which differs from that according to FIG. 1 in that a CCD sensor 5c is provided instead of the diaphragm 13, the lens 14 and the photodiode 5, said CCD sensor comprising measurement elements 21, pixels, shown in FIG. 5b. In order to form the measurement regions, only groups 22,23 of the measurement elements 21 are used for measurement. Depending on what shape is given to the measurement regions by respective selection of the groups 22,23 of the measurement elements 21, the evaluation is carried out in a manner analogous to that as described above with reference to FIGS. 1 to 4.

It goes without saying that a similar measurement result can also be achieved by virtue of the fact that two different CCD sensors, comprising if appropriate only a single line of sensor elements, could be formed one below the other.

It is pointed out that the invention can be realized by diverse different arrangements of beam paths. In this regard, it would be conceivable to provide dedicated light sources for each of the measurement regions. Furthermore, a dedicated sensor could be provided for each of the measurement regions, the measurements of which sensor are read out separately from one another by means of the evaluation unit. Furthermore, it would be conceivable for the light emerging from the light source 4 to be spatially separated from one another by mirrors in order to direct it onto one or a plurality of sensors in order to form the measurement regions.

The invention claimed is:

1. A device for measuring precipitation, comprising: a measuring chamber for receiving a precipitation particle; at least one light source for radiating light through the measuring chamber; and at least one sensor for sensing an intensity of the light radiating through the measuring chamber, wherein at least two measuring regions arranged one below another are provided in the measuring chamber and the intensity of the light radiating through each of the measuring regions is detectable separately, wherein the measuring regions have cross sections perpendicular to a radiation direction, the cross sections being of different sizes.

2. The device according to claim 1, wherein the at least two measuring regions are at a vertical distance from one another.

3. The device according to claim 1, further comprising an evaluation unit connected to the sensor so as to determine from the sensed light intensity a size, a shape, a volume, a speed of movement and/or a density of the precipitation particle.

4. The device according to claim 3, wherein the evaluation unit is configured to determine a snow moisture, a snow height forming on a substrate, a snow load and/or a risk of avalanche forming owing to precipitation.

5. The device according to claim 3, wherein the evaluation unit is configured to make a determination based on a change in the light intensity over time.

6. The device according to claim 3, wherein only a single sensor is provided for the at least two measuring regions and the evaluation unit is configured to assign intensity changes generated upon the passage of at least two of the precipitation particles at short time intervals to one of the precipitation particles.

7. The device according to claim 1, wherein the cross sections have different lengths in a vertical and/or in a horizontal direction.

8. The device according to claim 1, wherein, as viewed in a light radiation direction, at least one of the measuring regions projects beyond another of the measuring regions in a horizontal direction.

9. The device according to claim 8, wherein the at least one of the measuring regions projects beyond both sides of the another measuring region.

10. The device according to claim 8, wherein the one measuring region projects beyond the another measuring region in the horizontal direction to such an extent that the precipitation particle, if it merely grazes the another, narrower measuring region falls completely through the one, wider measuring region.

11. The device according to claim 10, wherein the one measuring region projects at least 1 cm beyond the another measuring region in the horizontal direction.

12. The device according to claim 11, wherein the one measuring region projects at least 2 cm beyond the another measuring region in the horizontal direction.

13. The device according to claim 1, further comprising a light source sensor for determining a standard signal generated by the light source on the sensor, a unit for measuring temperature and/or at least one scattered light sensor for determining scattering of the light at an optical component of the device.

14. A method for measuring precipitation, comprising the steps of: radiating light emerging from a light source through a measuring chamber that receives a precipitation particle; providing at least two measuring regions arranged one below another in the measuring chamber, wherein the measuring regions have cross sections perpendicular to a radiation direction, the cross sections being of different sizes; and sensing with a sensor an intensity of the light radiating through the measuring chamber including separately detecting the intensity of the light radiating through each of the measuring regions.

15. The method according to claim 14, further including determining a size, a shape, a volume, a speed of movement and/or a density of the precipitation particle, or/and of a snow moisture, a snow height forming on a substrate, a snow load and/or a risk of avalanche forming owing to precipitation based on the sensed intensity of light.

16. The method according to claim 14, wherein the cross sections have different lengths in a vertical and/or in a horizontal direction.

17. The method according to claim 14, wherein, as viewed in a light radiation direction, at least one of the measuring regions projects beyond both sides of another of the measuring regions in a horizontal direction.

* * * * *